(12) United States Patent
Kim (10) Patent No.: US 10,098,921 B2
(45) Date of Patent: Oct. 16, 2018

(54) **METHOD FOR TREATING GOUT AND GOUT-INDUCED ARTHRITIS USING COMPOSITION CONTAINING MIXED EXTRACT OF *CHRYSANTHEMUM INDICUM* AND *CINNAMOMUM CASSIA***

(71) Applicant: KOREA INSTITUTE OF ORIENTAL MEDICINE, Daejeon (KR)

(72) Inventor: Dong Seon Kim, Daejeon (KR)

(73) Assignee: KOREA INSTITUTE OF ORIENTAL MEDICINE, Daejeon (KR)

( * ) Notice: Subject to any disclaimer, the term of this patent is extended or adjusted under 35 U.S.C. 154(b) by 0 days.

(21) Appl. No.: 15/539,239

(22) PCT Filed: Dec. 18, 2015

(86) PCT No.: PCT/KR2015/013948
§ 371 (c)(1),
(2) Date: Jun. 23, 2017

(87) PCT Pub. No.: WO2016/105035
PCT Pub. Date: Jun. 30, 2016

(65) Prior Publication Data
US 2017/0354703 A1 Dec. 14, 2017

(30) Foreign Application Priority Data
Dec. 23, 2014 (KR) .......................... 10-2014-0187418

(51) Int. Cl.
| | |
|---|---|
| *A61K 36/28* | (2006.01) |
| *A61K 36/54* | (2006.01) |
| *A61K 36/287* | (2006.01) |
| *A23L 33/105* | (2016.01) |
| *A61P 19/06* | (2006.01) |
| *A61P 19/02* | (2006.01) |

(52) U.S. Cl.
CPC ............ *A61K 36/54* (2013.01); *A23L 33/105* (2016.08); *A61K 36/28* (2013.01); *A61K 36/287* (2013.01); *A61P 19/02* (2018.01); *A61P 19/06* (2018.01); *A61K 2300/00* (2013.01)

(58) Field of Classification Search
None
See application file for complete search history.

(56) References Cited

U.S. PATENT DOCUMENTS

| | | | |
|---|---|---|---|
| 2008/0038367 A1* | 2/2008 | Saloum | A61K 36/185 424/617 |
| 2011/0293754 A1 | 12/2011 | Lee et al. | |
| 2016/0220622 A1* | 8/2016 | Park | A61K 36/185 |
| 2016/0324776 A1* | 11/2016 | Glatzel | C08B 37/0015 |

FOREIGN PATENT DOCUMENTS

| | | |
|---|---|---|
| CN | 101732386 A | 6/2010 |
| CN | 101829264 A | 9/2010 |
| JP | 2002-121145 A | 4/2002 |
| KR | 10-2001-0018668 A | 3/2001 |
| KR | 10-0294091 B1 | 7/2001 |
| KR | 10-0429244 B1 | 4/2004 |
| KR | 10-2004-0080640 A | 9/2004 |
| KR | 10-0489267 B1 | 5/2005 |
| KR | 10-0842053 B1 | 6/2008 |
| KR | 10-2014-0106772 A | 9/2014 |

OTHER PUBLICATIONS

Nguyen M. et al. Xanthine Oxidase Inhibitory Activity of Vietnamese Medicinal Plants. Biological and Pharmaceutical Bulletin 27(9) 1414-1421, Sep. 2004. (Year: 2004).*
Nile S. et al. Screening of Ferulic Acid Related Compounds as Inhibitors of Xanthine Oxidase . . . Brazilian J of Pharmacognosy 26:50-55, 2016. (Year: 2016).*
Zhao, X. et al. Effects of Cassia Oil on Serum and Hepatic Uric Acid Levels . . . J of Ethnopharmacology 103:357-365, 2006. (Year: 2006).*
Lee, Y. et al. Synergistic Uric Acid Lowering Effects of the Combination of Chrysanthemum indicum Linne Flower . . . Evidence Based Complementary and Alternative Medicine 2017:1-9, 2017. (Year: 2017).*
Song, H. et al. Screening for Selective Inhibitors of Xanthine Oxidase From Flos Chrysanthemum . . . J of Chromatography B 961:56-61, May 14, 2014. (Year: 2014).*
Wang S. et al. Essential Oil From Leaves of Cinnamomum osmophloeum . . . Phytomedicine 15(11)940-945, Nov. 2008. (Year: 2008).*
Kong, L. et al. Inhibition of Xanthine Oxidase by Some Chinese Medicinal Plants Used to Treat Gout. J of Ethnopharmacology 73: 199-207, 2000. (Year: 2000).*
International Search Report for PCT/KR2015/013948.
L.D. Kong et al., "Inhibition of xanthine oxidase by some Chinese medicinal plants used to treat gout", Journal of Ethnopharmacology, vol. 73, pp. 199-207, 2000.
S.Y. Wang et al., "Essential oil from leaves of Cinnamomum osmophloeum acts as a xanthine oxidase inhibitor and reduces the serum uric acid levels in oxonate-induced mice", Phytomedicine, vol. 15, pp. 940-945, 2008.
F. Stirpe et al., "The Regulation of Rat Liver Xanthine Oxidase; Conversion in Vitro of the Enzyme Activity From Dehydrogenase (Type D) to Oxidase (Type 0)", The Journal of Biological Chemistry, vol. 244 (14), pp. 3855-3863, 1969.

(Continued)

*Primary Examiner* — Ralph J Gitomer
(74) *Attorney, Agent, or Firm* — The PL Law Group, PLLC (57) ABSTRACT

An anti-gout composition including the mixed extract of *Chrysanthemum indicum* and *Cinnamomum cassia* as an active ingredient shows substantially greater inhibitory effects on xanthine oxidase than when *Chrysanthemum indicum* or *Cinnamomum cassia* is used separately. An animal model treated with the mixed extract of *Chrysanthemum indicum* and *Cinnamomum cassia* experienced a decrease in uric acid in serum and in urine. The mixed extract of *Chrysanthemum indicum* and *Cinnamomum cassia* is an active ingredient induced from a natural material, and, accordingly, the mixed extract is safe and a source material therefor is easily provided. Accordingly, the mixed extract can be widely used in gout-related industries.

6 Claims, 4 Drawing Sheets

(56) References Cited

OTHER PUBLICATIONS

Office action dated Mar. 6, 2018 from Japan Intellectual Property Office in a counterpart Japanese Patent Application No. 2017-533009 (all the cited references are listed in this IDS.) (English translation is also submitted herewith.).

European Search Report for EP 15873562 from European patent office in a counterpart European patent application dated Jun. 20, 2018.

* cited by examiner

METHOD FOR TREATING GOUT AND GOUT-INDUCED ARTHRITIS USING COMPOSITION CONTAINING MIXED EXTRACT OF *CHRYSANTHEMUM INDICUM* AND *CINNAMOMUM CASSIA*

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2015/013948, filed Dec. 18, 2015, which claims priority to the benefit of Korean Patent Application No. 10-2014-0187418filed in the Korean Intellectual Property Office on Dec. 23, 2014, the entire contents of which are incorporated herein by reference.

TECHNICAL FIELD

The present invention relates to an anti-gout composition containing a mixed extract of *Chrysanthemum indicum* and *Cinnamomum cassia* as an active ingredient.

BACKGROUND ART

Gout refers to a disease that is caused by deposition of monosodium urate monohydrate crystals (MSU) in articular cartilage, tendons, or surrounding tissues. MSU are generated due to an increase in the uric acid content in blood, wherein the uric acid is the residue of body's metabolism regarding purine which is intaken through food. The causes of increased gouty arthritis include westernization of diet, increased obesity, aging of the population, increased prevalence of renal disease and hypertension, increased use of diuretics such as thiazide, and low-dose aspirin, etc.

In addition, gout is a very common inflammatory arthritis among male adults. It is known that the prevalence rate is about 1% to 2% in western countries, and the incidence of disease is lower in Asians compared to Westerners. However, recently, the prevalence rate has been increased in Western and Asian countries due to westernized eating habits and lifestyle. Even in South Korea, 9.3% of adults (14.3% of men, 2.2% of women) are found to have hyperuricemia. Gout is a type of adult disease that easily occurs in obese men. Uric acid increased in the blood is deposited in the form of MSU in the joints or surrounding tissues, causing inflammation, causing pain, swelling, and, in severe cases, deformation of joints. The disease progresses from the period during which the uric acid level in the blood is increased without symptoms, to the period during which acute intermittent arthritis develops and then chronic gouty arthritis develops with deformation of the joints.

Gout is known to have a clear and successful treatment therefor, but it is often accompanied by other diseases such as hypertension and chronic renal failure. Therefore, side effects of medication should be carefully considered, and, as a non-pharmacological treatment, patients' efforts to change their own lifestyles are essential for good prognosis in long-term treatment. Gout and hyperuricemia show clinical manifestations of hypertension, hyperlipidemia, hyperglycemia, and abdominal obesity. Although they are not the diagnostic criteria for the metabolic syndrome, which is a complex disorder that increases the risk of adult diseases such as arteriosclerotic heart disease and type 2 diabetes, gout and hyperuricemia seem to be closely related to the metabolic syndrome. In South Korea, it was reported that 44% of gout patients were accompanied by metabolic syndrome. Gout usually occurs in the form of acute monoarthritis, but, in some cases, may invade small number of joints or, rarely, multiple joints. Non-steroidal anti-inflammatory drugs (NSAIDs), which are used in the treatment of acute gout, are well known for inhibiting the inflammatory response; colchicine and steroids suppress the inflammatory response by inhibiting the activity and migration of leukocytes, and are all drugs that can effectively treat gout attacks; and selectively, cyclooxygenase (COX-2) inhibitors are known to have the same effect as existing non-steroidal anti-inflammatory drugs.

In addition, when the uric acid concentration in blood is maintained to a level below the saturation level for a long period of time, the size of existing gout tophi is reduced while acute gouty arthritis is prevented. In the chronic phase of gout, the treatment therefor is carried out to lower the concentration of uric acid in the blood. Uric acid-lowering agents are classified into a xanthine oxidase (XO) inhibitor and a uricosuric agent according to a mechanism. As uric acid-synthesis inhibitors, there are allopurinol, which is widely used, and febuxostat, which has been recently developed as a new drug. Allopurinol is an XO inhibitor that can be effectively used regardless of the cause of hyperuricemia, but the most serious side effect of allopurinol is hypersensitivity syndrome with fever, rash, an increase in eosinophils, hepatitis, renal failure, and the risk of death. Febuxostat is also known as XO inhibitor, but, unlike allopurinol, it is a nonpurine selective blocking agent that is metabolized mainly in the liver to form glucuronide. Most cases of gout progress into the chronic phase, and, even if there are no symptoms, in a prophylactic way, gout is treated by using anti-inflammatory drugs and a method of lowering the uric acid concentration. These prophylactic treatments should be used after the disease has been maintained for a period of time in a calm state, otherwise the gout will recur more severely. However, there is a lot of controversy about the clam period of the illness, and even such prophylactic treatments with existing drugs are not enough to prevent acute episodes of intermittent recurrence of gout, and the technology for inhibiting oxidase, which is a gout-inducing enzyme, with natural products is still insufficient.

Gout medicines need to be used chronically. Accordingly, side effects caused by cholchine or allopurinol cause serious problems. Therefore, it is necessary to research into and develop natural products that can prevent inflammation for a prolonged period without any side effects. However, the research and the development have not yet been actively performed. As an example of natural products known to date as research results, the extract of *Chrysanthemum indicum* disclosed in Patent No. 2014-0106772 is known to have a gout inhibitory effect.

Meanwhile, *Cinnamomum cassia* has been known to be effective as an herbal medicine for people with weak constitution and poor blood circulation to promote immunity (Korean Patent No. 0842053). Also, disclosed are a *Cinnamomum cassia* extract-containing composition for prevention and treatment of arteriosclerosis (Korea Patent No. 0294091), a cosmetic composition containing the extract of *Cinnamomum cassia* (Korean Patent Laid-Open No. 2001-0018668), and a composition for promoting oral hygiene containing a nanoparticulate *Cinnamomum cassia* extract (Korea Patent No. 0489267).

However, as shown according to the present invention, the enhanced effect on gout suppression of the anti-gout composition including the mixed extract of *Chrysanthemum indicum* and *Cinnamomum cassia* as an active ingredient has not been disclosed.

SUMMARY

The present invention has been made in view of the above-mentioned needs, and an object of the present invention is to provide an anti-gout composition which contains a mixed extract of *Chrysanthemum indicum* and *Cinnamomum cassia* as an active ingredient. More particularly, a xanthine oxidase inhibition rate of the mixed extract of *Chrysanthemum indicum* and *Cinnamomum cassia* was markedly improved as compared with when the extract of *Chrysanthemum indicum* or the extract of *Cinnamomum cassia* is used separately, thereby completing the present invention.

In order to achieve the above objects, the present invention provides an anti-gout composition which contains a mixed extract of *Chrysanthemum indicum* and *Cinnamomum cassia* as an active ingredient.

One or more embodiments of the present invention provide a health functional food for prevention or improvement of gout, containing the mixed extract of *Chrysanthemum indicum* and *Cinnamomum cassia* as an active ingredient.

One or more embodiments of the present invention provide a pharmaceutical composition for prevention or treatment of gout, containing the mixed extract of *Chrysanthemum indicum* and *Cinnamomum cassia* as an active ingredient.

One or more embodiments of the present invention provide a pharmaceutical composition for prevention or treatment of gout-induced arthritis, containing the mixed extract of *Chrysanthemum indicum* and *Cinnamomum cassia* as an active ingredient.

The present invention relates to an anti-gout composition containing a mixed extract of *Chrysanthemum indicum* and *Cinnamomum cassia*. The composition inhibits xanthine oxidase, which is a gout-inducing enzyme, and reduces the amount of uric acid in urine, thereby preventing, improving or treating gout.

BRIEF DESCRIPTION OF THE DRAWINGS

FIG. 3 shows the results obtained by confirming the amount of uric acid contained in the urine according to the treatment of 100 mg/kg/day of the *Chrysanthemum indicum* extract, 100 mg/kg/day of the *Cinnamomum cassia* extract, and 100 mg/kg/day of the mixed extract of *Chrysanthemum indicum* and *Cinnamomum cassia* according to the present invention. * and *** indicate that there is a statistically significant difference in the amount of uric acid in the urine among the allopurinol treatment group, a *Chrysanthemum indicum* extract treatment group, a *Cinnamomum cassia* extract treatment group, and a group treated with various concentrations of the mixed extract of *Chrysanthemum indicum* and *Cinnamomum cassia*, these groups being compared with a hyperuricemia-induced group; and in the case of *, the p value is less than 0.05, and in the case of ***, the p value is less than 0.001.

FIG. 4 shows the results obtained by confirming the amount of uric acid contained in serum according to the treatment of 100 mg/kg/day of the *Chrysanthemum indicum* extract, 100 mg/kg/day of the *Cinnamomum cassia* extract, and 100 mg/kg/day of the mixed extract of *Chrysanthemum indicum* and *Cinnamomum cassia* according to the present invention. * and *** indicate that there is a statistically significant difference in the amount of uric acid in serum among the allopurinol treatment group, a *Chrysanthemum indicum* extract treatment group, a *Cinnamomum cassia* extract treatment group, and a group treated with various concentrations of the mixed extract of *Chrysanthemum indicum* and *Cinnamomum cassia*, these groups being compared with a hyperuricemia-induced group; and in the case of *, the p value is less than 0.05, and in the case of ***, the p value is less than 0.001.

DETAILED DESCRIPTION

One or more embodiments of the present invention provide an anti-gout composition containing a mixed extract of *Chrysanthemum indicum* and *Cinnamomum cassia* as an active ingredient.

The mixed extract of *Chrysanthemum indicum* and *Cinnamomum cassia* may be obtained by using water, ethanol, or a mixed solvent thereof, but is not limited thereto. In one embodiment, a mixture weight ratio of *Chrysanthemum indicum* extract and *Cinnamomum cassia* extract in the mixed extract may be in a range of 1:0.1 to 1:10, for example, 1:1.

The mixed extract of *Chrysanthemum indicum* and *Cinnamomum cassia* according to the present invention may be obtained by obtaining *Chrysanthemum indicum* extract and *Cinnamomum cassia* extract separately and then mixing those extracts. However, in other embodiments, *Chrysanthemum indicum* and *Cinnamomum cassia* may be mixed, and then, the mixture is subjected to an extracting process to obtain the mixed extract of *Chrysanthemum indicum* and *Cinnamomum cassia* according to the present invention.

*Chrysanthemum indicum* used herein refer to every part of the plant including flowers, leaves, stems and roots, and *Cinnamomum cassia* refers to a medicinal material made of a bark of Japanese Cinnamon.

The mixed extract of *Chrysanthemum indicum* and *Cinnamomum cassia* inhibits xanthine oxidase.

Another aspect of the present invention provides a health functional food for prevention or improvement of gout, containing the mixed extract of *Chrysanthemum indicum* and *Cinnamomum cassia* as an active ingredient.

The health functional food for prevention or improvement of gout containing the mixed extract of *Chrysanthemum indicum* and *Cinnamomum cassia* may be prepared in any form selected from beverage, pill, tablet, capsule, and powder, or may be prepared by adding the mixed extract to other food or ingredients of food, and may be suitably prepared according to a conventional method.

Examples of the foods to which the mixed extract of *Chrysanthemum indicum* and *Cinnamomum cassia* is to be added, include meat, sausage, bread, chocolate, candy, snack, confectionery, pizza, instant noodles, other noodles, gum, dairy products including ice cream, soups, beverages, tea, drinks, alcoholic beverages, and vitamin complexes. The foods used herein refer to any food that is considered as a health-supplementary food in a conventional sense.

The health functional foods may include various nutrients, vitamins, minerals (electrolytes), synthetic and natural flavors, colorants and enhancers (cheese, chocolate etc.), pectic acid and its salts, alkynic acid and its salts, organic acids, protective colloid thickeners, pH adjusting agents, stabilizers, preservatives, glycerin, alcohols, carbonating agents used in carbonated drinks, and the like. The health functional foods may also include natural fruit juices and fruit flesh for the production of vegetable drinks. These components may be used independently or in combination.

The health functional food according to the present invention may further contain various flavors or natural carbohydrates as an additional ingredient. Examples of the natural carbohydrates include monosaccharides such as glucose and fructose, disaccharides such as maltose and sucrose, and polysaccharides such as dextrin and cyclodextrin, and sugar alcohols such as xylitol, sorbitol, and erythritol. As a sweetening agent, natural sweetening agents such as thaumatin and stevia extract, or synthetic sweetening agents such as saccharin and aspartame may be used.

Another aspect of the present invention provides a pharmaceutical composition for prevention or treatment of gout containing the mixed extract of *Chrysanthemum indicum* and *Cinnamomum cassia* as an active ingredient. The pharmaceutical composition according to the present invention may further include a carrier, an excipient, or a diluent in addition to the mixed extract of *Chrysanthemum indicum* and *Cinnamomum cassia*. Examples of the carrier, excipient and diluent which may be included in the pharmaceutical composition according to the present invention, include lactose, dextrose, sucrose, sorbitol, mannitol, xylitol, erythritol, maltitol, starch, acacia rubber, alginate, gelatin, calcium phosphate, calcium silicate , cellulose, methylcellulose, microcrystalline cellulose, polyvinylpyrrolidone, water, methylhydroxybenzoate, propylhydroxybenzoate, talc, and magnesium stearate. However, the examples of the carrier, excipient and diluent are not limited thereto.

In addition, the pharmaceutical composition may be administered orally or parenterally in a conventional manner. When the pharmaceutical composition is formulated, a diluent or excipient, such as a filler, an extender, a binder, a wetting agent, a disintegrant, a surfactant, or the like, may be used in the formulation process. Solid formulations for oral administration include tablets, pills, powder, granules, capsules and the like, and these solid formulations are prepared by mixing with at least one excipient selected from starch, calcium carbonate, sucrose, lactose, gelatin, and the like. In addition to simple excipients, lubricants such as magnesium stearate and talc may also be used. Liquid formulations for oral administration include suspensions, solutions, emulsions, syrups and the like. Various excipients, such as wetting agents, sweeteners, fragrances, preservatives and the like, may be included in addition to water and liquid paraffin, which are simple diluents commonly used. Formulations for parenteral administration include sterile aqueous solutions, non-aqueous solutions, suspensions, emulsions, freeze-dried preparations, and suppositories. Examples of the non-aqueous solvent and the suspending agent include propylene glycol, polyethylene glycol, vegetable oil such as olive oil, injectable ester such as ethyl oleate, and the like. Examples of suppository bases include witepsol, macrogol, tween 61, cacao paper, laurin, glycerogelatin, and the like.

Another aspect of the present invention provides a pharmaceutical composition for prevention or treatment of gout-induced arthritis containing the mixed extract of *Chrysanthemum indicum* and *Cinnamomum cassia* as an active ingredient.

Hereinafter, the present invention will be described in more detail with reference to Examples. Those skilled in the art may understand that these examples are only for describing the present invention in detail and that the scope of the present invention is not limited thereto.

EXAMPLE 1

Preparation of Mixed Ethanol Extract of *Chrysanthemum indicum* and *Cinnamomum cassia*

15 l of 70% ethanol was added to 1 kg of *Chrysanthemum indicum* and 1 kg of *Cinnamomum cassia*, separately, and each of the mixtures was subjected to an extraction process at a temperature of 85□ for 3 hours. Filtrates obtained therefrom were concentrated under reduced pressure at 50□, thereby obtaining 95 g of *Chrysanthemum indicum* ethanol extract and 77 g of *Cinnamomum cassia* ethanol extract. The *Chrysanthemum indicum* ethanol extract and the *Cinnamomum cassia* ethanol extract were mixed at a weight ratio of 1:1 to prepare a mixed ethanol extract of *Chrysanthemum indicum* and *Cinnamomum cassia*.

EXAMPLE 2

Preparation of Mixed Water Extract of *Chrysanthemum indicum* and *Cinnamomum cassia*

15 l of purified water was added to 1 kg of *Chrysanthemum indicum* and 1 kg of *Cinnamomum cassia*, separately, and each of the mixtures was subjected to an extraction process at a temperature of 100□ for 3 hours. Filtrates obtained therefrom were concentrated under reduced pressure at 55□, thereby obtaining 146 g of *Chrysanthemum indicum* ethanol extract and 110 g of *Cinnamomum cassia* ethanol extract. The *Chrysanthemum indicum* water extract and the
*Cinnamomum cassia* water extract were mixed at a weight ratio of 1:1 to prepare a mixed water extract of *Chrysanthemum indicum* and *Cinnamomum cassia*.

EXAMPLE 3

Inhibitory Activity of Mixed Ethanol Extract of *Chrysanthemum indicum* and *Cinnamomum cassia* on Xanthine Oxidase Inhibitory activity of the mixed ethanol extract of *Chrysanthemum indicum* and *Cinnamomum cassia* prepared according to Example 1 on xanthine oxidase was analyzed. The inhibitory activity of xanthine oxidase was analyzed by using the method presented by Sirpe and Della Corte [Stirpe F, Della Corte E. 1969. The regulation of rat liver xanthine oxidase. *J Biol Chem* 244: 3855-3563].

Figure 1:
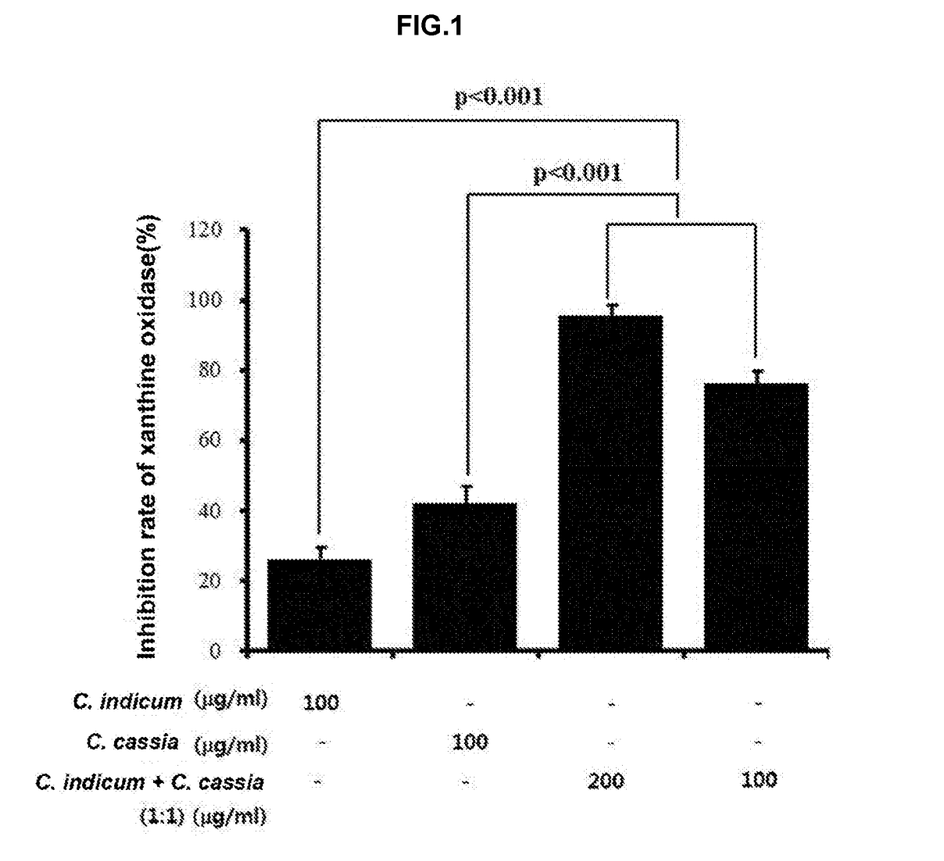
FIG. 1 shows the results obtained by confirming the inhibitory activity of a mixed extract of *Chrysanthemum indicum* (*C. indicum*) and *Cinnamomum cassia* (*C. cassia*) according to the present invention on xanthine oxidase.

The mixed extract prepared according to Example 1 was diluted 5-fold and then 0.2 ml of a substrate solution, obtained by dissolving 2 mM of xanthine in 0.1 ml of the diluted solution and 0.6 ml of 0.1 M potassium phosphate buffer (pH 7.5), was added thereto. 0.1 ml of xanthine oxidase (0.2 U/ml) was added thereto and the reaction was carried out at 37□ for 5 minutes. Then, 1 ml of 1N HCl was added to stop the reaction, and the absorbance of uric acid produced in the reaction solution was measured at a wavelength of 292 nm. The inhibitory activity of the mixed extract on xanthine oxidase was shown by the percentage (%) of the absorbance reduction in a group treated with or without a sample. As a control, instead of the mixed extract, the *Chrysanthemum indicum* ethanol extract and the *Cinnamomum cassia* ethanol extract were each diluted in the same manner as applied to the mixed extract, and their inhibitory activities on xanthine oxidase were measured in the same manner as used for the mixed extract. Results obtained therefrom are shown in FIG. 1.

As a result, it was confirmed that, compared with when the same concentration of the *Chrysanthemum indicum* extract or *Cinnamomum cassia* extract was used separately, the mixed extract of *Chrysanthemum indicum* and *Cinnamomum cassia* showed a statistically significant synergistic inhibitory activity on xanthine oxidase.

EXAMPLE 4

Uric Acid-Reducing Effects in Urine of Gout-Induced Animal Model

Potassium oxonate (150 mg/kg, 0.5% sodium carboxymethylcellulose (CMC-Na with 0.1 M sodium acetate, pH 5)) was intraperitoneally injected to SD-rats, which is a gout animal model, to induce hyperuricemia. After 24 hours, urine was collected from the rats, and hyperacidemia-induced rats were selected therefrom using a QuantiChrom™ Uric Acid Assay Kit (DIUA-250, BioAssay Systems, USA). 200 mg/kg, 100 mg/kg, and 50 mg/kg of mixed extracts of *Chrysanthemum indicum* and *Cinnamomum cassia* (1:1) were administered to the selected experimental animals. Similarly, as a positive control, 50 mg/kg allopurinol was suspended in a 0.01 M PBS buffer containing 0.1% polyoxyethylene sorbitan monolate, and the result was orally administered for 3 days and, on the day just before the autopsy, the rats were fasted for 16 hours. After the last oral administration, urine was collected for 2 hours, and the rats were anesthetized with ethyl ether and the blood was taken therefrom. The amount of urine acid in the blood was measured using a QuantiChrom ™ Uric Acid Assay kit (DIUA-250, BioAssay Systems, USA).

Figure 2:
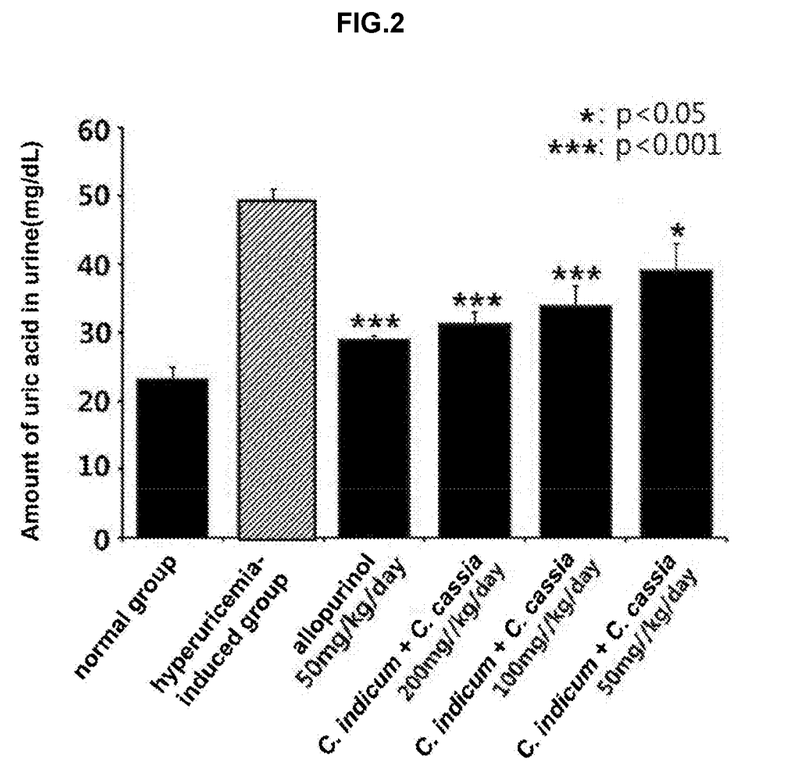
FIG. 2 shows the results obtained by confirming the amount of uric acid contained in the urine according to the treatments of 50, 100, and 200 mg/kg/day of the mixed extract of *Chrysanthemum indicum* and *Cinnamomum cassia* according to the present invention. * and *** indicate that there is a statistically significant difference in the amount of uric acid in the urine between a group treated with allopurinol and a group treated with 50, 100, or 200 mg/kg/day of the mixed extract of *Chrysanthemum indicum* and *Cinnamomum cassia*, these groups being compared with a hyperuricemia-induced group; and in the case of *, the p value is less than 0.05, and in the case of ***, the p value is less than 0.001.

As shown in FIG. 2, the amount of uric acid in the urine was increased to about 50 mg/dL by the administration of potassium oxonate, and due to the administration of the mixed extract of *Chrysanthemum indicum* and *Cinnamomum cassia* according to the present invention, the amount of uric acid was decreased to about 32 mg/dL, showing effects similar to those obtained by using allopurinol, which is a positive control.

EXAMPLE 5

Synergistic Effect of *Chrysanthemum indicum* Extract and *Cinnamomum cassia* Extract on Reduction of Uric Acid in Blood and Urine of Gout-Induced Animal Model Potassium oxonate (150 mg/kg, 0.5% sodium carboxymethylcellulose (CMC-Na with 0.1 M sodium acetate, pH 5)) was intraperitoneally injected to SD-rats, which is a gout animal model, of gout to induce hyperuricemia. After 24 hours, urine was collected from the rats, and hyperacidemia-induced rats were selected therefrom using a QuantiChrom™ Uric Acid Assay Kit (DIUA-250, BioAssay Systems, USA). 100 mg/kg of the *Chrysanthemum indicum* extract, 100 mg/kg of the *Cinnamomum cassia* extract, and 100 mg/kg of the mixed extract of *Chrysanthemum indicum* and *Cinnamomum cassia* (1:1) were administered to the selected experimental animals. Similarly, as a positive control, 50 mg/kg allopurinol was suspended in a 0.01 M PBS buffer containing 0.1% polyoxyethylene sorbitan monolate, and the result was orally administered for 3 days and, on the day just before the autopsy, the rats were fasted for 16 hours. After the last oral administration, urine was collected for 2 hours, and the rats were anesthetized with ethyl ether and the blood was taken therefrom. The amount of urine acid in the blood was measured using a QuantiChrom ™ Uric Acid Assay kit (DIUA-250, BioAssay Systems, USA).

Figure 3:
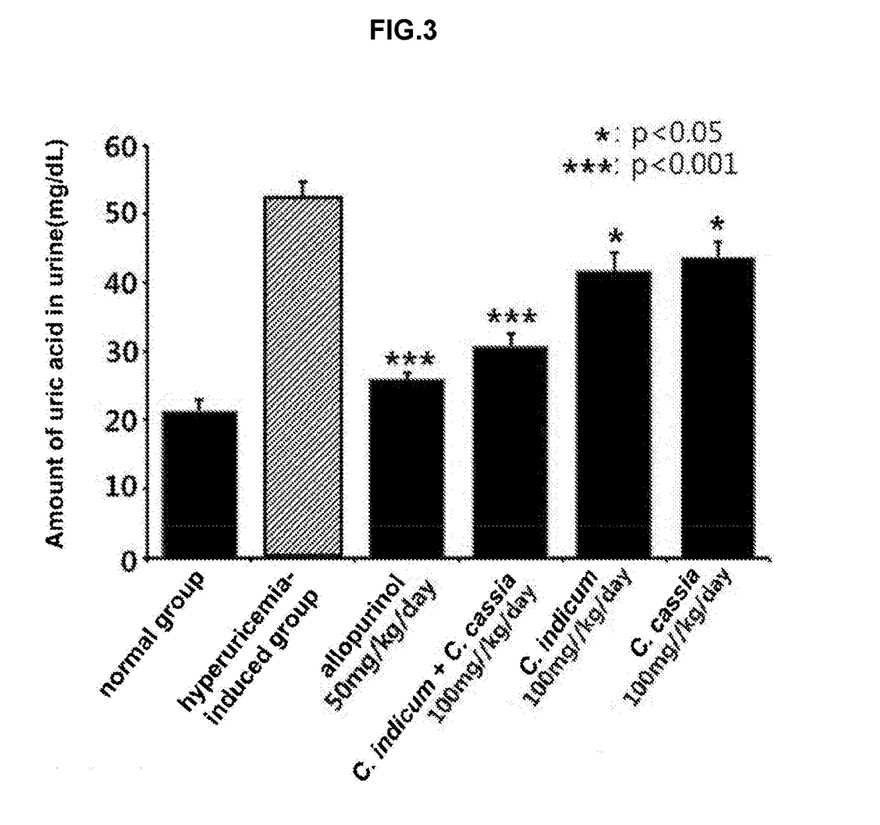

As shown in FIG. 3, the amount of uric acid in the urine was increased to about 53 mg/dL by the administration of potassium oxonate, and due to the administration of the mixed extract of *Chrysanthemum indicum* and *Cinnamomum cassia* according to the present invention, the amount of uric acid was decreased to about 31 mg/dL, showing effects similar to those obtained by using allopurinol, which is a positive control. On the other hand, the *Chrysanthemum indicum* extract and the *Cinnamomum cassia* extract lead to a decrease to 42 mg/dL and 44 mg/dL, respectively. That is, the reduction effect of each of these extracts was smaller than that of the mixed extract of *Chrysanthemum indicum* and *Cinnamomum cassia*. Accordingly, it was confirmed that the mixing of the *Chrysanthemum indicum* extract and the *Cinnamomum cassia* extract contributed to the synergistic effect.

Figure 4:
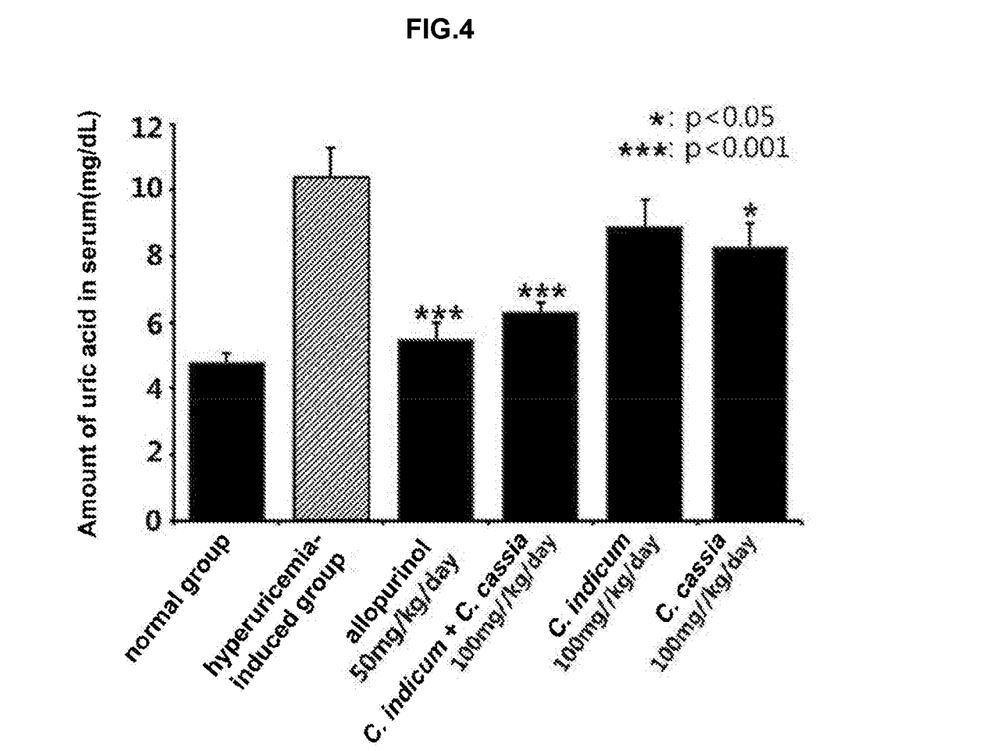

As shown in FIG. 4, the amount of uric acid in the blood was increased to about 10.4 mg/dL by the administration of potassium oxonate, and due to the administration of the mixed extract of *Chrysanthemum indicum* and *Cinnamomum cassia* according to the present invention, the amount of uric acid was decreased to about 6.3 mg/dL, showing effects similar to those obtained by using allopurinol, which is a positive control. On the other hand, the *Chrysanthemum indicum* extract and the *Cinnamomum cassia* extract lead to decreases of 8.9 mg/dL and 8.3 mg/dL, respectively. That is, the reduction effect of each of these extracts were smaller than those of the mixed extract of *Chrysanthemum indicum* and *Cinnamomum cassia*. Accordingly, it was confirmed that the mixing of the *Chrysanthemum indicum* extract and the *Cinnamomum cassia* extract contributed to the synergistic effect.

The invention claimed is:

1. A method for treating gout in a subject, the method comprising:
   administering to the subject having gout a therapeutic amount of a composition comprising a mixed extract of *Chrysanthemum indicum* extract and *Cinnamomum cassia* extract at a weight ratio of 1:0.1 to 1:10 as an active ingredient.

2. The method of claim 1, wherein the composition further comprises an additive selected from the group consisting of a carrier, an excipient, and a diluent.

3. The method of claim 1, wherein the mixed extract is prepared by using a solvent selected from the group consisting of water and/or ethanol to obtain the *Chrysanthemum indicum* extract and the *Cinnamomum cassia* extract and mixing the *Chrysanthemum indicum* extract and the *Cinnamomum cassia* extract.

4. A method for treating gout-induced arthritis in a subject, the method comprising:
   administering to the subject having gout-induced arthritis a therapeutic amount of a composition comprising a mixed extract of *Chrysanthemum indicum* extract and *Cinnamomum cassia* extract at a weight ratio of 1:0.1 to 1:10 as an active ingredient.

5. The method of claim 4, wherein the composition further comprises an additive selected from the group consisting of a carrier, an excipient, and a diluent.

6. The method of claim 4, wherein the mixed extract is prepared by using a solvent selected from the group consisting of water and/or ethanol to obtain the *Chrysanthemum indicum* extract and the *Cinnamomum cassia* extract and mixing the *Chrysanthemum indicum* extract and the *Cinnamomum cassia* extract.

\* \* \* \* \*